United States Patent [19]
Krämer et al.

[11] Patent Number: 5,464,809
[45] Date of Patent: Nov. 7, 1995

[54] FUNGICIDAL 2-METHOXIMINOCARBOXYLIC ESTERS

[75] Inventors: Wolfgang Krämer, Burscheid; Dieter Berg, Wuppertal; Heinz-Wilhelm Dehne, Monheim; Stefan Dutzmann, Hilden, all of Germany

[73] Assignee: Bayer Aktiengesellschaft, Leverkusen, Germany

[21] Appl. No.: 304,756

[22] Filed: Sep. 12, 1994

Related U.S. Application Data

[62] Division of Ser. No. 163,495, Dec. 7, 1993, Pat. No. 5,380,914, which is a division of Ser. No. 709,937, Jun. 4, 1991, Pat. No. 5,312,960.

[30] Foreign Application Priority Data

Jun. 16, 1990 [DE] Germany ............... 40 19 307.1

[51] Int. Cl.$^6$ ................................. A01N 43/66
[52] U.S. Cl. ............... 504/227; 504/240; 504/242; 504/287; 504/290; 504/315; 544/249; 544/301; 544/218; 546/326; 548/134; 548/135; 560/35
[58] Field of Search ............... 560/35; 504/227, 504/242, 317, 315, 296, 292; 544/218, 319, 316, 249, 301, 218; 549/398, 464; 546/326; 548/135, 134

[56] References Cited

U.S. PATENT DOCUMENTS 5,312,960  5/1994  Kramer et al. ............... 560/35

*Primary Examiner*—Josè Dees
*Assistant Examiner*—Samuel Bartz
*Attorney, Agent, or Firm*—Sprung Horn Kramer & Woods

[57] ABSTRACT

Fungicidal new 2-methoximinocarboxylic esters of the general formula (I)

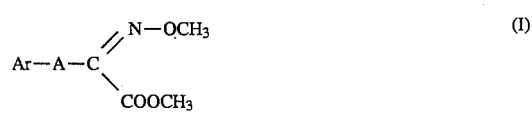

in which
Ar represents one of the radicals

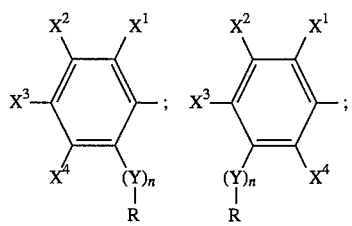

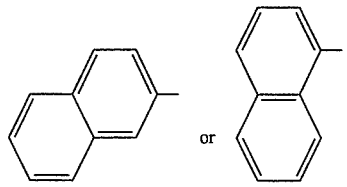

and

A represents one of the radicals —$CH_2$—;

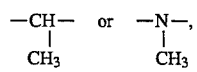

where
Y represents one of the radicals

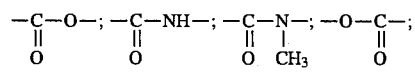

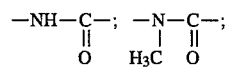

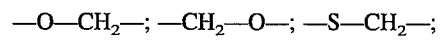

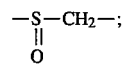

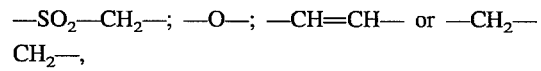

n represents the number 0 or 1,

R represents alkyl, halogenoalkyl, alkenyl, halogenoalkenyl, or represents optionally substituted cycloalkyl, or represents optionally substituted aryl or represents optionally substituted heteroaryl, and, moreover, in the event that n is 0, also represents halogen, and $X^1$, $X^2$, $X^3$ and $X^4$ independently of one another in each case represent hydrogen, halogen, hydroxyl or methoxy, but where, in the event that $X^2$ represents bromine, $X^3$ does not simultaneously represent hydroxyl or methoxy.

8 Claims, No Drawings

FUNGICIDAL 2-METHOXIMINOCARBOXYLIC ESTERS

This is a division of application Ser. No. 08/163,495 filed on Dec. 7, 1993, now U.S. Pat. No. 5,380,914, which is a division of application Ser. No. 07/709,937, filed Jun. 4, 1991, now U.S. Pat. No. 5,312,960.

The invention relates to new 2-methoximinocarboxylic esters, to several processes for their preparation, and to their use as pesticides.

It is known that certain carboxylic esters such as, for example, the compound methyl 3-methoxy-2-(2-methylphenyl)-acrylate, have fungicidal activity (compare, for example, European Patent 178,826).

However, the activity of these previously known compounds is not entirely satisfactory in all fields of application, in particular when low amounts and concentrations are used.

Furthermore, certain 2-methoximinocarboxylic esters are known (compare, for example, Tetrahedron Lett. 23, 3699–3702 [1982]; Tetrahedron Lett. 22, 3247–3248 [1981]; Austral. J. Chem. 34, 765–768 [1981]; Tetrahedron Lett. 21, 2277–2280 [1980]; J. Chem. Soc., Perkin Trans. 1, 1975, 2340–2348; Experientia 31, 756–757 [1975]; J. Chem. Soc., Perkin Trans. 1, 1972, 18–24). Nothing has been known to date about an activity of these previously known compounds as pesticides.

New 2-methoximinocarboxylic esters have been found, of the general formula (I),

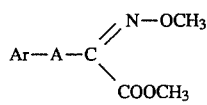

(I)

in which

Ar represents one of the radicals

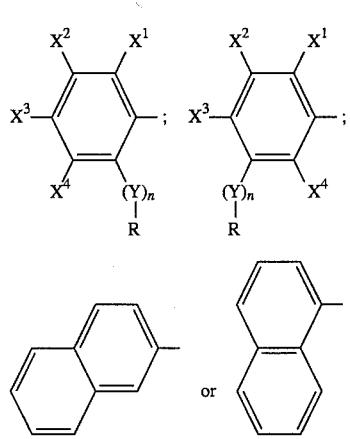

and

A represents one of the radicals —$CH_2$—;

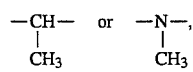

where

Y represents one of the radicals

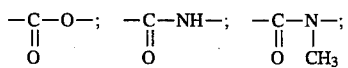

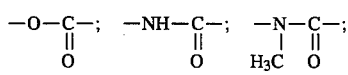

—O—$CH_2$—; —$CH_2$—O—; —S—$CH_2$—;

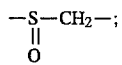

—$SO_2$—$CH_2$—; —O—; —CH=CH— or —$CH_2$—$CH_2$—, n represents the number 0 or 1, R represents alkyl, halogenoalkyl, alkenyl, halogenoalkenyl, or represents optionally substituted cycloalkyl, or represents optionally substituted aryl or represents optionally substituted heteroaryl, and, moreover, in the event that n is 0, also represents halogen, and $X^1$, $X^2$, $X^3$ and $X^4$ independently of one another in each case represent hydrogen, halogen, hydroxyl or methoxy, but where, in the event that $X^2$ represents bromine, $X^3$ does not simultaneously represent hydroxyl or methoxy.

The compounds of the formula (I) can be in the form of geometric isomers or mixtures of isomers of various compositions. The invention claims the pure isomers and also the mixtures of isomers.

Furthermore, it has been found that the new 2-methoximinocarboxylic esters of the general formula (I),

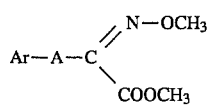

(I)

in which

Ar represents one of the radicals

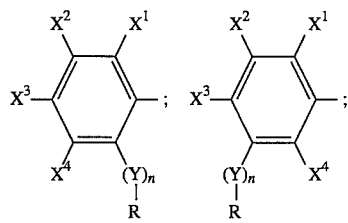

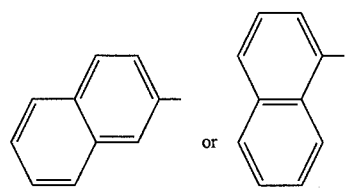

and

A represents one of the radicals —$CH_2$—;

$$-\overset{|}{\underset{CH_3}{CH}}- \quad \text{or} \quad -\overset{|}{\underset{CH_3}{N}}-,$$

where

Y represents one of the radicals $$-\underset{O}{\overset{\|}{C}}-O-; \quad -\underset{O}{\overset{\|}{C}}-NH-; \quad -\underset{O}{\overset{\|}{C}}-\underset{CH_3}{\overset{|}{N}}-;$$

$$-O-\underset{O}{\overset{\|}{C}}-; \quad -NH-\underset{O}{\overset{\|}{C}}-; \quad -\underset{H_3C}{\overset{|}{N}}-\underset{O}{\overset{\|}{C}}-;$$

$$-O-CH_2-; \quad -CH_2-O-; \quad -S-CH_2-;$$

$$-\underset{O}{\overset{\|}{S}}-CH_2-;$$

$$-SO_2-CH_2-; \quad -O-; \quad -CH=CH- \quad \text{or} \quad -CH_2-CH_2-,$$

n represents the number 0 or 1,

R represents alkyl, halogenoalkyl, alkenyl, halogenoalkenyl, or represents optionally substituted cycloalkyl, or represents optionally substituted aryl or represents optionally substituted heteroaryl, and, moreover, in the event that n is 0, also represents halogen, and $X^1$, $X^2$, $X^3$ and $X^4$ independently of one another in each case represent hydrogen, halogen, hydroxyl or methoxy, but where, in the event that $X^2$ represents bromine, $X^3$ does not simultaneously represent hydroxyl or methoxy, are obtained by one of the processes described below:

(a) 2-methoximinocarboxylic esters of the formula (Ia), $$Ar-\underset{R^1}{\overset{|}{CH}}-C\overset{\displaystyle N-OCH_3}{\underset{\displaystyle COOCH_3}{\diagdown}} \qquad (Ia)$$

in which $R^1$ represents hydrogen or methyl and

Ar has the abovementioned meaning, are obtained when acrylic ester derivatives of the formula (II), $$Ar-\underset{R^1}{\overset{|}{C}}=C\overset{\displaystyle NH-\underset{O}{\overset{\|}{C}}-CH_3}{\underset{\displaystyle COOCH_3}{\diagdown}} \qquad (II)$$

in which $R^1$ and Ar have the abovementioned meanings, are reacted with an acid addition salt of O-methylhydroxylamine, if appropriate in the presence of a diluent and if appropriate in the presence of a reaction auxiliary;

(b) 2-methoximinocarboxylic esters of the formula (Ib), $$Ar-\underset{CH_3}{\overset{|}{N}}-C\overset{\displaystyle N-OCH_3}{\underset{\displaystyle COOCH_3}{\diagdown}} \qquad (Ib)$$

in which

Ar has the abovementioned meaning, are obtained when, in a first step, aromatic amines of the formula (III), $$Ar-NH-CH_3 \qquad (III)$$

in which

Ar has the abovementioned meaning, are first reacted with methyl 2-chloro-2-hydroximinoacetate of the formula (IV)

$$Cl-C\overset{\displaystyle N-OH}{\underset{\displaystyle COOCH_3}{\diagdown}} \qquad (IV)$$

if appropriate in the presence of a diluent and if appropriate in the presence of an acid-binding agent, and, in a second step, the product is subsequently methylated on the hydroximino group using a methylation agent, if appropriate in the presence of an acid-binding agent;

(c) 2-methoximinocarboxylic esters of the formula (Ic), $$Ar^1-\underset{R^1}{\overset{|}{CH}}-C\overset{\displaystyle N-OCH_3}{\underset{\displaystyle COOCH_3}{\diagdown}} \qquad (Ic)$$

in which

R1 represents hydrogen or methyl and $Ar^1$ represents one of the radicals

[two substituted benzene ring structures with positions labeled $X^1$, $X^2$, $X^3$, $X^4$, $Y^1$, R]

where $Y^1$ in each case represents one of the radicals $$-\underset{O}{\overset{\|}{C}}-O-; \quad -\underset{O}{\overset{\|}{C}}-NH- \quad \text{or} \quad -\underset{O}{\overset{\|}{C}}-\underset{CH_3}{\overset{|}{N}}-$$

and $X^1$, $X^2$, $X^3$, $X^4$ and R have the abovementioned meanings, are alternatively also obtained when substituted phenol or aniline derivatives of the formula (V),

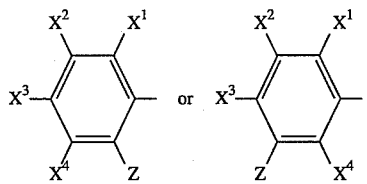

(V)

in which

R¹ represents hydrogen or methyl and
Ar² represents one of the radicals

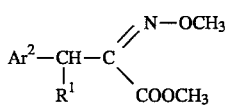

where

Z in each case represents hydroxyl, amino or N-methylamino and

X¹, X², X³ and X⁴ have the abovementioned meanings, are acylated with acid chlorides of the formula (VI),

(VI)

in which

R has the abovementioned meaning, if appropriate in the presence of a diluent and if appropriate in the presence of an acid-binding agent.

Finally, it has been found that the new 2-methoximinocarboxylic esters of the general formula (I) have a highly pronounced activity against pests.

Surprisingly, the 2-methoximinocarboxylic esters of the general formula (I) according to the invention show considerably better fungicidal activity than the carboxylic esters known from the prior art, such as, for example, the compound methyl 3-methoxy-2-(2-methylphenyl)-acrylate, which are similar compounds chemically and from the point of view of their action.

Formula (I) provides a general definition of the 2-methoximinocarboxylic esters according to the invention.

In the definitions mentioned under the general formula (I),

R preferably represents straight-chain or branched alkyl having 1 to 8 carbon atoms, straight-chain or branched halogenoalkyl having 1 to 8 carbon atoms and 1 to 9 identical or different halogen atoms, straight-chain or branched alkenyl having 2 to 8 carbon atoms, straight-chain or branched halogenoalkenyl having 2 to 8 carbon atoms and 1 to 9 identical or different halogen atoms, or represents cycloalkyl which has 3 to 7 carbon atoms and which is optionally monosubstituted or polysubstituted by identical or different substituents from the series comprising halogen and/or straight-chain or branched alkyl having 1 to 6 carbon atoms, or represents heteroaryl which has 2 to 9 carbon atoms and 1 to 5 identical or different hetero atoms—in particular nitrogen, oxygen and/or sulphur—and which is optionally monosubstituted or polysubstituted by identical or different substituents, suitable heteroaryl substituents in each case being: halogen and in each case straight-chain or branched alkyl or alkoxy each of which has 1 to 6 carbon atoms; or R furthermore preferably represents aryl which has 6 to 10 carbon atoms and which is optionally monosubstituted or polysubstituted by identical or different substituents, suitable aryl substituents being: halogen, cyano, nitro, in each case straight-chain or branched alkyl, alkoxy, alkylthio, alkylsulphinyl or alkylsulphonyl each of which has 1 to 6 carbon atoms, in each case straight-chain or branched alkenyl, alkynyl, alkenyloxy, alkynyloxy, alkenylthio or alkynylthio each of which has 2 to 6 carbon atoms, in each case straight-chain or branched halogenoalkyl, halogenoalkoxy, halogenoalkylthio, halogenoalkylsulphinyl and halogenoalkylsulphonyl each of which has 1 to 6 carbon atoms and 1 to 13 identical or different halogen atoms, in each case straight-chain or branched halogenoalkenyl, halogenoalkynyl, halogenoalkenyloxy, halogenoalkynyloxy, halogenoalkenylthio or halogenoalkynylthio each of which has 2 to 6 carbon atoms and 1 to 9 identical or different halogen atoms, in each case straight-chain or branched alkylcarbonyl, alkoxycarbonyl, alkylcarbonyloxy, alkylcarbonylamino, alkylcarbonyl-(N-alkyl)-amino, aminocarbonyl, N-alkyl-aminocarbonyl, N,N-dialkylaminocarbonyl or alkoximinoalkyl each of which has 1 to 6 carbon atoms in the individual alkyl moieties, and aryl, aryloxy, arylthio, arylcarbonyl, arylcarbonyloxy, arylcarbonylamino, arylcarbonyl-(N-alkyl)amino, arylaminocarbonyl, N-aryl-N-alkylaminocarbonyl, arylalkyl or arylalkenyl each of which has 6 to 10 carbon atoms in the aryl moiety and, if appropriate, up to 6 carbon atoms in the individual alkyl or alkenyl moieties and each of which is optionally monosubstituted or polysubstituted by identical or different substituents, suitable substituents in the individual aryl moieties in each case being: halogen, cyano, nitro, in each case straight-chain or branched alkyl, alkoxy, alkylthio, alkylsulphinyl, or alkylsulphonyl each of which has 1 to 6 carbon atoms, in each case straight-chain or branched alkenyl, alkynyl, alkenyloxy, alkynyloxy, alkenylthio or alkynylthio each of which has 2 to 6 carbon atoms, in each case straight-chain or branched halogenoalkyl, halogenoalkoxy, halogenoalkylthio, halogenoalkylsulphinyl and halogenoalkylsulphonyl each of which has 1 to 6 carbon atoms and 1 to 13 identical or different halogen atoms, in each case straight-chain or branched halogenoalkenyl, halogenoalkynyl, halogenoalkenyloxy, halogenoalkynyloxy, halogenoalkenylthio or halogenoalkynylthio each of which has 2 to 6 carbon atoms and 2 to 9 identical or different halogen atoms, in each case straight-chain or branched alkylcarbonyl, alkoxycarbonyl, alkylcarbonyloxy, alkylcarbonylamino, alkylcarbonyl-(N-alkyl)-amino, aminocarbonyl, N-alkyl-aminocarbonyl, N,N-dialkylaminocarbonyl or alkoximinoalkyl each of which has 1 to 6 carbon atoms in the individual alkyl moieties, and aryl, aryloxy, arylthio, arylcarbonyl, arylcarbonyloxy, arylcarbonylamino, arylcarbonyl-(N-alkyl)amino, arylaminocarbonyl, N-aryl-N-alkylaminocarbonyl, arylalkyl or arylalkenyl each of which has 6 to 10 carbon atoms in the aryl moiety and if appropriate up to 6 carbon atoms in the individual alkyl or alkenyl moieties and each of which is optionally monosubstituted or polysubstituted by identical or different substituents, suitable substituents in the individual aryl moieties in each case being: halogen and in each case straight-chain or branched alkyl or alkoxy each of which has 1 to 6 carbon atoms;

in the event that n is 0, R furthermore preferably also represents fluorine, chlorine, bromine or iodine.

In the definitions mentioned under the general formula (I),

R particularly preferably represents straight-chain or branched alkyl having 1 to 6 carbon atoms, straight-chain or branched halogenoalkyl having 1 to 6 carbon atoms and 1 to 9 identical or different halogen atoms, straight-chain or branched alkenyl having 2 to 6 carbon atoms, straight-chain or branched halogenoalkenyl having 2 to 6 carbon atoms and 1 to 9 identical or different halogen atoms, cycloalkyl which has 3 to 7 carbon atoms and which is optionally monosubstituted to pentasubstituted by identical or different substituents from the series comprising straight-chain or branched alkyl having 1 to 4 carbon atoms and/or halogen, or heteroaryl which has 2 to 9 carbon atoms and 1 to 4 identical or different hetero atoms—in particular nitrogen, oxygen and/or sulphur—and which is optionally monosubstituted to trisubstituted by identical or different substituents, suitable heteroaryl substituents in each case being: fluorine, chlorine, bromine and in each case straight-chain or branched alkyl or alkoxy each of which has 1 to 4 carbon atoms; or R moreover particularly preferably represents aryl which has 6 or 10 carbon atoms and which is optionally monosubstituted to pentasubstituted by identical or different substituents, suitable aryl substituents in each case being: fluorine, chlorine, bromine, cyano, nitro, in each case straight-chain or branched alkyl, alkoxy, alkylthio, alkylsulphinyl or alkylsulphonyl each of which has 1 to 4 carbon atoms, in each case straight-chain or branched alkenyl, alkynyl, alkenyloxy, alkynyloxy, alkenylthio or alkynylthio each of which has 2 to 4 carbon atoms, in each case straight-chain or branched halogenoalkyl, halogenoalkoxy, halogenoalkylthio, halogenoalkylsulphinyl and halogenoalkylsulphonyl each of which has 1 to 4 carbon atoms and 1 to 9 identical or different halogen atoms, in each case straight-chain or branched halogenoalkenyl, halogenoalkynyl, halogenoalkenyloxy, halogenoalkynyloxy, halogenoalkenylthio or halogenoalkynylthio each of which has 2 to 4 carbon atoms and 1 to 7 identical or different halogen atoms, in each case straight-chain or branched alkylcarbonyl, alkoxycarbonyl, alkylcarbonyloxy, alkylcarbonylamino, alkylcarbonyl-(N-alkyl)-amino, aminocarbonyl, N-alkyl-aminocarbonyl, N,N-dialkylaminocarbonyl or alkoximinoalkyl each of which has 1 to 4 carbon atoms in the individual alkyl moieties, and aryl, aryloxy, arylthio, arylcarbonyl, arylcarbonyloxy, arylcarbonylamino, arylcarbonyl-(N-alkyl)amino, arylaminocarbonyl, N-aryl-N-alkylaminocarbonyl, arylalkyl or arylalkenyl each of which has 6 to 10 carbon atoms in the aryl moiety and if appropriate up to 4 carbon atoms in the individual alkyl or alkenyl moieties and each of which is optionally monosubstituted or polysubstituted by identical or different substituents, suitable substituents in the individual aryl moieties in each case being: fluorine, chlorine, bromine, cyano, nitro, in each case straight-chain or branched alkyl, alkoxy, alkylthio, alkylsulphinyl or alkylsulphonyl each of which has 1 to 4 carbon atoms, in each case straight-chain or branched alkenyl, alkynyl, alkenyloxy, alkynyloxy, alkenylthio or alkynylthio each of which has 2 to 4 carbon atoms, in each case straight-chain or branched halogenoalkyl, halogenoalkoxy, halogenoalkylthio, halogenoalkylsulphinyl and halogenoalkylsulphonyl each of which has 1 to 4 carbon atoms and 1 to 9 identical or different halogen atoms, in each case straight-chain or branched halogenoalkenyl, halogenoalkynyl, halogenoalkenyloxy, halogenoalkynyloxy, halogenoalkenylthio or halogenoalkynylthio each of which has 2 to 4 carbon atoms and 1 to 7 identical or different halogen atoms, in each case straight-chain or branched alkylcarbonyl, alkoxycarbonyl, alkylcarbonyloxy, alkylcarbonylamino, alkylcarbonyl-(N-alkyl)-amino, aminocarbonyl, N-alkyl-aminocarbonyl, N,N-dialkylaminocarbonyl or alkoximinoalkyl each of which has 1 to 4 carbon atoms in the individual alkyl moieties, and aryl, aryloxy, arylthio, arylcarbonyl, arylcarbonyloxy, arylcarbonylamino, arylcarbonyl-(N-alkyl)amino, arylaminocarbonyl, N-aryl-N-alkylaminocarbonyl, arylalkyl or arylalkenyl each of which has 6 to 10 carbon atoms in the aryl moiety and if appropriate up to 4 carbon atoms in the individual alkyl or alkenyl moieties and each of which is optionally monosubstituted or polysubstituted by identical or different substituents, suitable substituents in the individual aryl moieties in each case being: fluorine, chlorine, bromine and in each case straight-chain or branched alkyl or alkoxy each of which has 1 to 4 carbon atoms; or in the event that n is 0, R furthermore particularly preferably also represents chlorine or bromine.

Moreover, $X^1$, $X^2$, $X^3$ and $X^4$ independently of one another in each case preferably represent hydrogen, fluorine, chlorine, bromine, iodine, hydroxyl or methoxy, but where, in the event that $X^2$ represents bromine, $X^3$ does not simultaneously represent hydroxyl or methoxy.

In particular, $X^1$, $X^2$, $X^3$ and $X^4$ independently of one another in each case represent hydrogen, chlorine, bromine, hydroxyl or methoxy, but where, in the event that $X^2$ represents bromine, $X^3$ does not simultaneously represent hydroxyl or methoxy.

In the definitions listed under the general formula (I), Ar preferably represents the radical

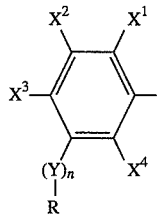

where

R, Y, n, $X^1$, $X^2$, $X^3$ and $X^4$ can have the meanings indicated above.

If, for example, methyl 2-acetamido-3-[3-(4-chlorophenyl)-phenyl]-acrylate and O-methylhydroxylamine hydrochloride are used as starting substances, the course of the reaction of process (a) according to the invention can be outlined by the following equation:

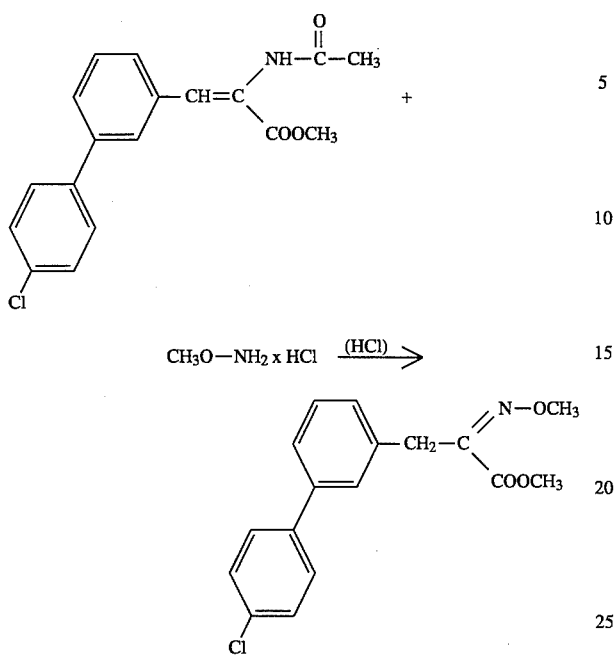

If, for example, methyl 2-chloro-2-hydroximinoacetate and N-methyl-3-trifluoromethylaniline are used as starting substances and dimethyl sulphate as methylating agent, the course of the reaction of process (b) according to the invention can be outlined by the following equation:

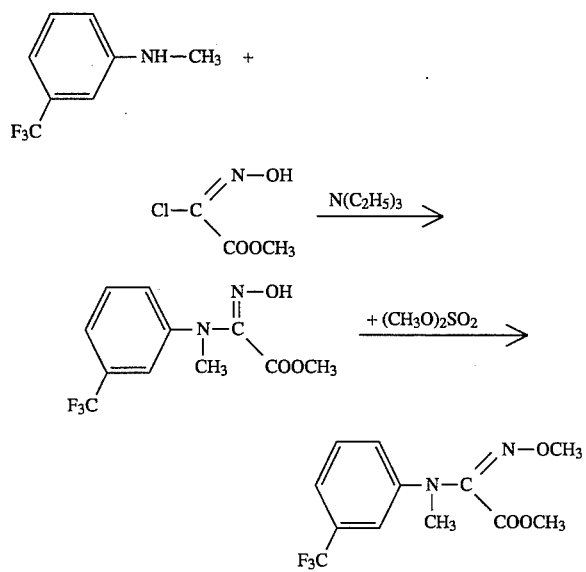

If, for example, methyl 3-(3-hydroxyphenyl)-2-methoximino-propionate and 3-chlorobenzoyl chloride are used as starting substances, the course of the reaction of process (c) according to the invention can be outlined by the following equation:

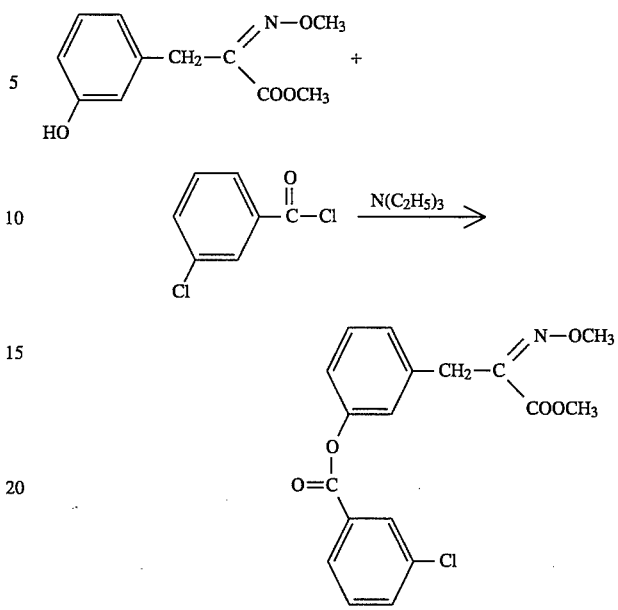

Formula (II) provides a general definition of the acrylic ester derivatives required as starting substances for carrying out process (a) according to the invention. In this formula (II), Ar preferably represents those radicals which have already been mentioned in connection with the description of the substances of the formula (I) according to the invention as being preferred for these substituents.

$R^1$ preferably represents hydrogen or methyl. The acrylic ester derivatives of the formula (II) are known (compare, for example, Synthesis 1989, 414–418; Jpn. Kokai Tokkyo Koho JP 61218558; J. Labelled Comp. Radiopharm. 21, 263– 284 [1984]; Liebigs Ann. Chem. 1984, 1205–1215) or can be obtained in analogy to known processes (compare, for example, Organic Reactions Vol. III, Azlactones p. 198–239), for example when aromatic aldehydes or ketones of the formula (VII),

 (VII)

in which $R^1$ and Ar have the abovementioned meanings,
are reacted with N-acetylglycine in the presence of acetic anhydride and sodium acetate and if appropriate in the presence of acetic acid at temperatures between 20° C. and 160° C. and then, in a second step, the resulting azlactones of the formula (VIII),

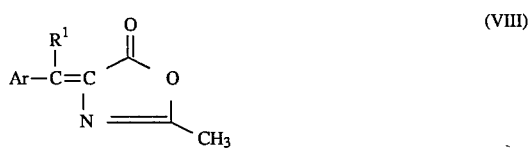 (VIII)

in which $R^1$ and Ar have the abovementioned meanings,
are reacted in methanol, if appropriate in the presence of a base such as, for example, sodium hydroxide or sodium methylate, at temperatures between 0° C. and 50° C.

Aromatic aldehydes and ketones of the formula (VII) are generally known compounds of organic chemistry or can be obtained in analogy to generally known processes.

Formula (III) provides a general definition of the aromatic amines required as starting substances for carrying out process (b) according to the invention. In this formula (III), Ar preferably represents those radicals which have already been mentioned in connection with the description of the substances of the formula (I) according to the invention as being preferred for these substituents.

The aromatic amines of the formula (III) are likewise generally known compounds of organic chemistry.

Methyl 2-chloro-2-hydroximino-acetate, of the formula (IV), which is furthermore required as a starting compound for carrying out process (b) according to the invention, is likewise known (compare DE 1,963,061; U.S. Pat. No. 3,584,032).

Formula (V) provides a general definition of the substituted phenol and aniline derivatives required as starting substances for carrying out process (c) according to the invention. In this formula (V), $R^1$ preferably represents hydrogen or methyl and $Ar^2$ represents one of the radicals

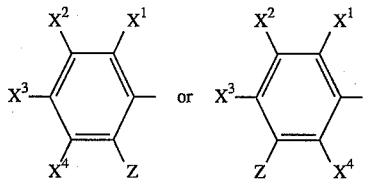

Z in each case represents hydroxyl, amino or N-methylamino and $X^1$, $X^2$, $X^3$ and $X^4$ preferably represent those radicals which have already been mentioned in connection with the description of the substances of the formula (I) according to the invention as being preferred for these substituents.

The substituted phenol and aniline derivatives of the formula (V) were hitherto unknown and are likewise a subject of the invention.

They are obtained when azlactones of the formula (IX),

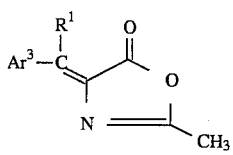

in which $R^1$ has the abovementioned meaning and $Ar^3$ represents one of the radicals

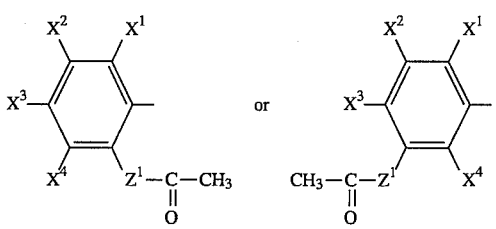

where $Z^1$ in each case represents oxygen, an NH group or an

group and $X^1$, $X^2$, $X^3$ and $X^4$ have the abovementioned meanings, are reacted with methanol in the presence of a base such as, for example, sodium hydroxide and subsequently in the presence of an acid such as, for example, hydrochloric acid, at temperatures between 0° C. and 50° C., and the resulting acrylic ester derivatives of the formula (X),

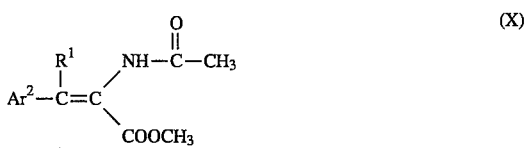

in which $R^1$ has the abovementioned meaning and $Ar^2$ represents one of the radicals

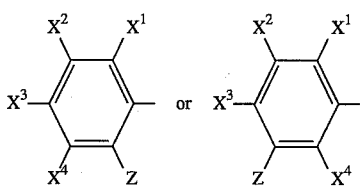

where

Z in each case represents hydroxyl, amino or N-methylamino and $X^1$, $X^2$, $X^3$ and $X^4$ have the abovementioned meanings, are subsequently reacted with an acid addition salt of O-methylhydroxylamine such as, for example, O-methylhydroxylamine hydrochloride, if appropriate in the presence of a diluent such as, for example, methanol and if appropriate in the presence of a reaction auxiliary such as, for example, sulphuric acid, in analogy to the procedure of process (a) according to the invention at temperatures between 20° C. and 60° C.

Azlactones of the formula (IX) are known (compare, for example, Takeda Kenkyushoho 43, 53–76 [1984]; Izv. Akad. Nauk SSSR, Ser. Khim. 1984, 1090–1094; Izv. Akad. Nauk SSSR, Ser. Khim. 1980, 823–829; Tetrahedron Lett. 1979, 737–740; Bull. Soc. Chim. Belg., 83 (3/4), 117–132 [1974]; DE 2,243,665; BE 715,588; ZA 6803 083) or can be obtained in analogy to known processes (compare, for example, Organic Reactions Vol. III, Azlactones, p. 108–239).

Formula (VI) provides a general definition of the acid chlorides furthermore required as starting substances for carrying out process (c) according to the invention. In this formula (VI), R preferably represents those radicals which have already been mentioned in connection with the description of the substances of the formula (I) according to the invention as being preferred for this substituent.

The acid chlorides (VI) are generally known compounds of organic chemistry.

Suitable diluents for carrying out process (a) according to the invention are polar organic solvents or aqueous systems. Diluents which are particularly preferably used are alcohols such as, for example, methanol, ethanol or propanol, their mixtures with water, or pure water.

Suitable reaction auxiliaries for carrying out process (a) according to the invention are strong mineral acids such as hydrochloric acid, hydrobromic acid or sulphuric acid.

When carrying out process (a) according to the invention, the reaction temperatures can be varied within a substantial range. In general, the process is carried out at temperatures between 0° C. and 100° C., preferably at temperatures between 20° C. and 60° C.

For carrying out process (a) according to the invention, 1.0 to 3.0 moles, preferably 1.0 to 1.5 moles, of O-methylhydroxylamine and, if appropriate, 1.0 to 3.0 moles, preferably 1.0 to 1.5 moles, of reaction auxiliary are generally employed per mole of acrylic ester derivative of the formula (II). The reaction is carried out and the reaction products are worked up and isolated by generally customary methods (compare also the preparation examples).

Suitable diluents for carrying out process (b) according to the invention, both for step 1 and for step 2, are inert organic solvents. These include, in particular, aliphatic, alicyclic or aromatic, optionally halogenated hydrocarbons such as, for example, benzine, benzene, toluene, xylene, chlorobenzene, petroleum ether, hexane, cyclohexane, dichloromethane, tetrachloroethane, chloroform, carbon tetrachloride, ethers such as diethyl ether, dioxane, tetrahydrofuran or ethylene glycol dimethyl ether or ethylene glycol diethyl ether, ketones such as acetone or butanone, nitriles such as acetonitrile or propionitrile, amides such as dimethylformamide, dimethylacetamide, N-methylformanilide, N-methylpyrrolidone or hexamethylphosphoric triamide, esters such as ethyl acetate, or sulphoxides such as dimethyl sulphoxide.

Process (b) according to the invention is preferably carried out in the presence of a suitable acid-binding agent. Suitable acid-binding agents, both for step 1 and also for step 2, are all inorganic and organic bases which can customarily be used. The following are preferably used: the hydrides, hydroxides, amides, alcoholates, carbonates or hydrogen carbonates of alkali metals such as, for example, sodium hydride, sodium amide, sodium hydroxide, sodium methylate, sodium ethylate, potassium t-butylate, sodium carbonate or sodium hydrogen carbonate, and also tertiary amines such as, for example, triethylamine, N,N-dimethylaniline, pyridine, N,N-dimethylaminopyridine, diazabicyclooctane (DABCO), diazabicyclononene (DBN) or diazabicycloundecene (DBU).

When carrying out step 1 of process (b) according to the invention, the reaction temperatures can be varied in a substantial range. In general, the process is carried out at temperatures between −20° C. and 100° C., preferably at temperatures between 0° C. and 80° C.

For carrying out step 1 of process (b) according to the invention, 1.0 to 1.5 moles, preferably 1.0 to 1.2 moles, of methyl 2-chloro-2-hydroximinoacetate, of the formula (IV), and, if appropriate, 1.0 to 1.5 moles, preferably 1.0 to 1.2 moles, of acid-binding agent are generally employed per mole of aromatic amine of the formula (III). The reaction is carried out and the reaction products are worked up and isolated by generally customary methods.

Suitable methylating agents for carrying out step 2 of process (b) according to the invention are all the methylating agents which can customarily be used. The following are preferably used: dimethyl sulphate, methyl p-toluenesulphonate, methyl iodide or methyl bromide. Dimethyl sulphate is particularly suitable.

When carrying out step 2 of process (b) according to the invention, the reaction temperatures can be varied within a substantial range. In general, the process is carried out at temperatures between −20° C. and 100° C., preferably at temperatures between 0° C. and 80° C.

For carrying out step 2 of process (b) according to the invention, 1.0 to 1.5 moles, preferably 1.0 to 1.2 moles, of methylating agents and, if appropriate, 1.0 to 1.5 moles, preferably 1.0 to 1.2 moles, of acid-binding agent are generally employed per mole of hydroximino starting compound. The reaction is carried out and the reaction products are worked up and isolated by generally customary methods (compare also the preparation examples).

Suitable diluents for carrying out process (c) according to the invention are inert organic solvents. These include, in particular, aliphatic, alicyclic or aromatic, optionally halogenated hydrocarbons such as, for example, benzine, benzene, toluene, xylene, chlorobenzene, petroleum ether, hexane, cyclohexane, dichloromethane, chloroform, carbon tetrachloride, ethers such as diethyl ether, dioxane, tetrahydrofuran or ethylene glycol dimethyl ether or ethylene glycol diethyl ether, ketones such as acetone or butanone, nitriles such as acetonitrile or propionitrile, amides such as dimethylformamide, dimethylacetamide, N-methylformanilide, N-methylpyrrolidone or hexamethylphosphoric triamide, esters such as ethyl acetate, or sulphoxides such as dimethyl sulphoxide.

Process (c) according to the invention is preferably carried out in the presence of a suitable acid-binding agent. Suitable acid-binding agents are all the customary inorganic or organic bases. These include, for example, alkali metal hydroxides such as sodium hydroxide or potassium hydroxide, alkali metal carbonates such as sodium carbonate, potassium carbonate or sodium hydrogen carbonate, and also tertiary amines such as triethylamine, N,N-dimethylaniline, pyridine, N,N-dimethylaminopyridine, diazabicyclooctane (DABCO), diazabicyclononene (DBN) or diazabicycloundecene (DBU).

When carrying out process (c) according to the invention, the reaction temperatures can be varied within a substantial range. In general, the process is carried out at temperatures between −20° C. and 100° C., preferably at temperatures between 0° C. and 60° C.

For carrying out process (c) according to the invention, 1.0 to 1.5 moles, preferably 1.0 to 1.2 moles, of acid chloride of the formula (VI) and, if appropriate, 1.0 to 1.5 moles, preferably 1.0 to 1.2 moles, of acid-binding agent are generally employed per mole of phenol or aniline derivative of the formula (V).

The reaction is carried out and the reaction products are worked up and isolated by generally customary methods (compare also the preparation examples).

The active compounds according to the invention have a powerful action against pests and can be employed in practice for combating undesired harmful organisms. The active substances are suitable for use as plant protection agents, in particular as fungicides.

Fungicidal agents in plant protection are employed for combating Plasmodiophoromycetes, Oomycetes, Chytridiomycetes, Zygomycetes, Ascomycetes, Basidiomycetes and Deuteromycetes.

Some causative organisms of fungal diseases which come under the generic names listed above may be mentioned as examples, but not by way of limitation:

Pythium species, such as, for example, *Pythium ultimum;*
Phytophthora species, such as, for example, Phytophthora infestans;
Pseudoperonospora species, such as, for example, *Pseudoperonospora humuli* or *Pseudoperonospora cubensis;*

Plasmopara species, such as, for example, *Plasmopara viticola;*

Peronospora species, such as, for example, *Peronospora pisi* or *P. brassicae;*

Erysiphe species, such as, for example, *Erysiphe graminis;*

Sphaerotheca species, such as, for example, *Sphaerotheca fuliginea;*

Podosphaera species, such as, for example, *Podosphaera leucotricha;*

Venturia species, such as, for example, *Venturia inaequalis;*

Pyrenophora species, such as, for example, *Pyrenophora teres* or *P. graminea* (conidia form: Drechslera, syn: Helminthosporium);

Cochliobolus species, such as, for example, *Cochliobolus sativus* (conidia form: Drechslera, syn: Helminthosporium);

Uromyces species, such as, for example, *Uromyces appendiculatus;*

Puccinia species, such as, for example, *Puccinia recondita;*

Tilletia species, such as, for example, *Tilletia caries;*

Ustilago species, such as, for example, *Ustilago nuda* or *Ustilago avenae;*

Pellicularia species, such as, for example, *Pellicularia sasakii;*

Pyricularia species, such as, for example, *Pyricularia oryzae;*

Fusarium species, such as, for example, *Fusarium culmorum;*

Botrytis species, such as, for example, *Botrytis cinerea;*

Septoria species, such as, for example, *Septoria nodorum;*

Leptosphaeria species, such as, for example, *Leptosphaeria nodorum;*

Cercospora species, such as, for example, *Cercospora canescens;*

Alternaria species, such as, for example, *Alternaria brassicae* and

Pseudocercosporella species, such as, for example, *Pseudocercosporella herpotrichoides.*

The good toleration, by plants, of the active compounds, at the concentrations required for combating plant diseases, permits treatment of above-ground parts of plants, of vegetative propagation stock and seeds, and of the soil.

In this context, the active compounds according to the invention can be employed with particularly good success for combating cereal diseases such as, for example, against the causative organism of powdery mildew of cereals (*Erysiphe graminis*) on barley or wheat, or against the causative organism of net blotch disease of barley (*Pyrenophora teres*) or against the causative organism of brown spot (*Cochliobolus sativus*) on barley or wheat, or against the causative organism of brown blotch of wheat (*Leptosphaeria nodorum*) or against the causative organism of snow mold of cereals (*Fusarium nivale*), or for combating rice diseases such as, for example, against the causative organism of rice blast disease (*Pyricularia oryzae*), or for combating diseases in fruit growing and vegetable growing, such as, for example, against the causative organism of apple scab (*Venturia inaequalis*).

Depending on their particular physical and/or chemical properties, the active compounds can be converted into the customary formulations, such as solutions, emulsions, suspensions, powders, foams, pastes, granules, aerosols, very fine capsules in polymeric substances and in coating compositions for seed, as well as ULV cold-mist and warm-mist formulations.

These formulations are produced in a known manner, for example by mixing the active compounds with extenders, that is, liquid solvents, liquefied gases under pressure, and/or solid carriers, optionally with the use of surface-active agents, that is, emulsifying agents and/or dispersing agents and/or foam-forming agents. In the case of the use of water as an extender, organic solvents can, for example, also be used as auxiliary solvents. As liquid solvents, there are suitable in the main: aromatics, such as xylene, toluene, or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water; by liquefied gaseous extenders or carriers are meant liquids which are gaseous at ambient temperature and under atmospheric pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly-disperse silica, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumin hydrolysis products; as dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention can be present in the formulations as a mixture with other known active compounds, such as fungicides, insecticides, acaricides and herbicides, as well as in mixtures with fertilisers and growth regulators.

The active compounds can be used as such or in the form of their formulations or the use forms prepared therefrom, such as ready-to-use solutions, suspensions, wettable powders, pastes, soluble powders, dusts and granules. They are used in the customary manner, for example by watering, spraying, atomizing, scattering, dusting, foaming, brushing on and the like. It is furthermore possible to apply the active compounds by the ultra-low volume method or to inject the active compound formulation or the active compound itself into the soil. The seeds of the plants can also be treated.

In the treatment of parts of plants, the active compound concentrations in the use forms can be varied within a substantial range. They are, in general, between 1 and 0.0001% by weight, preferably between 0.5 and 0.001%. In the treatment of seed, amounts of active compound of 0.001 to 50 g per kilogram of seed, preferably 0.01 to 10 g, are generally required.

In the treatment of soil, active compound concentrations of 0.00001 to 0.1% by weight, preferably 0.0001 to 0.02% by weight, are required at the place of action.

PREPARATION EXAMPLES

Example 1

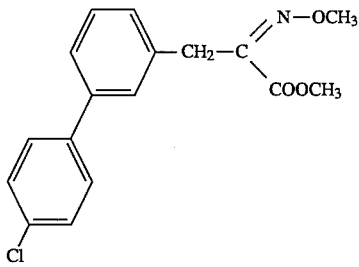

(Process a)

To a suspension of 130 g (0.395 mol) of methyl 2-acetamido- 3-[3-(4-chlorophenyl)-phenyl]-acrylate in 500 ml of methanol there are added 36 g (0.435 mol) of O-methylhydroxylamine hydrochloride and 43.5 ml (0.435 mol) of concentrated hydrochloric acid, the mixture is refluxed for 38 hours and then concentrated in vacuo, the residue is taken up in 1 l of dichloromethane, the mixture is washed three times using 500 ml of water each time and dried over sodium sulphate, the solvent is removed in vacuo, and the residue is purified by chromatography on silica gel (eluent: dichloromethane).

104.2 g (83% of theory) of methyl 3-[3-(4-chlorophenyl)-phenyl]-2-methoximinopropionate are obtained as an oil of refractive index $n_D^{23}$ of 1.5919.

PREPARATION OF THE STARTING COMPOUND

Example II-1

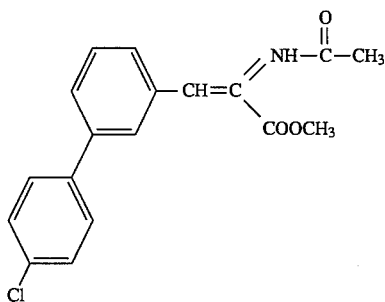

To a suspension of 130 g (0.437 mol) of 4-[3-(4-chlorophenyl)-benzylidene]- 2-methyl-1,3-oxazolin-5-one in 500 ml of methanol there are added 1.7 ml (0.022 mol) of 50 percent strength aqueous sodium hydroxide solution, and the mixture is then stirred for 18 hours at 20° C. For working up, the solid which has precipitated is filtered off with suction, washed with 200 ml of diethyl ether and dried.

130 g (90% of theory) of methyl 2-acetamido-3-[3-(4-chlorophenyl)-phenyl]-acrylate of melting point 168° C. are obtained.

Example VIII-1

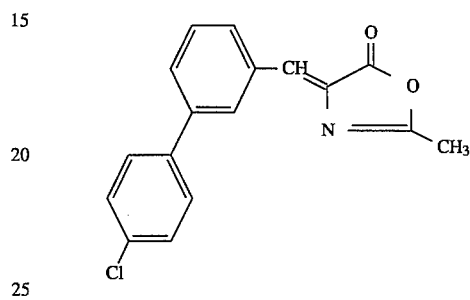

To a suspension of 179 g (0.827 mol) of 3-(4-chlorophenyl)-benzaldehyde in 1 l of acetic anhydride there are added 117.1 g (1 mol) of N-acetylglycine and 82 g (1 mol) of sodium acetate, and the mixture is stirred for 18 hours at 130° C. For working up, the solvent is distilled off under a water pump vacuum, the residue is taken up in 2 l of dichloromethane, the mixture is washed three times using 1 l of water each time, dried over sodium sulphate and concentrated in vacuo. The residue is crystallized by stirring with 300 ml of acetonitrile, filtered off with suction and dried.

115.9 g (47% of theory) of 4-[3-(4-chlorophenyl)benzylidene]-2-methyl-1,3-oxazolin-5-one of melting point 150° C. are obtained.

Example 2

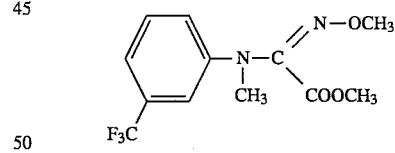

(Process b)

To 0.5 g (0.0018 mol) of methyl 2-(hydroximino)-2-[N-methyl-N-( 3-trifluoromethylphenyl)-amino]-acetate in 30 ml of tetrahydrofuran there are added 0.3 g (0.0018 mol) of potassium carbonate and 0.2 ml (0.0018 mol) of dimethyl sulphate, the mixture is stirred for 16 hours at 20° C., the solid which has precipitated is then filtered off with suction, the filtrate is concentrated under a water pump vacuum, and the residue is chromatographed over silica gel (eluent: toluene/ethyl acetate 1:1).

0.5 g (100% of theory) of methyl 2-methoximino-2-[N-methyl-N-( 3-trifluoromethylphenyl)-amino]-acetate are obtained as an oil.

$^1$H-NMR (CDCl$_3$/tetramethylsilane): δ=4.12 (3H,s); 3.66 (3H,s); 3.22 (3H,s)ppm

PREPARATION OF THE STARTING COMPOUND

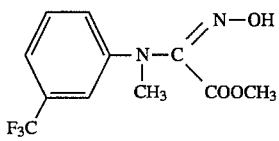

To 6.8 g (0.039 mol) of N-methyl-3-trifluoromethylaniline in 50 ml of toluene there are added 5.4 ml (0.039 mol) of triethylamine and subsequently at 5° C., dropwise and with stirring, a solution of 5.4 g (0.039 mol) of methyl 2-chloro- 2-hydroximino acetate in 17 g of toluene. The mixture is allowed to stand for 16 hours at room temperature, then washed twice with 50 ml of water each time, dried over sodium sulphate and concentrated in vacuo and the residue is chromatographed on silica gel (eluent: toluene/ ethyl acetate 1:1).

0.5 g (4.6% of theory) of methyl 2-hydroximino-2-[N-methyl-N-( 3-trifluoromethylphenyl)-amino]-acetate of melting point 131° C. are obtained.

Example 3

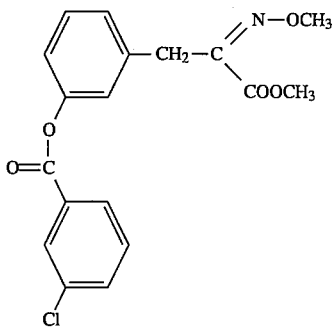

(Process c)

To 4.4 g (0.02 mol) of methyl 3-(3-hydroxyphenyl)-2-methoximinopropionate and 2.8 ml (0.02 mol) of triethylamine in 20 ml of ethyl acetate there are added dropwise in the course of 10 minutes at room temperature 3.5 g (0.02 mol) of 3-chlorobenzoyl chloride in 10 ml of ethyl acetate, during which the temperature of the reaction mixture rises to 30° C. The mixture is stirred for one hour at room temperature and then washed twice using 100 ml of water each time, dried over sodium sulphate and concentrated in vacuo, and the residue is crystallized by stirring with 20 ml of n-hexane, filtered off with suction and dried.

5.2 g (72% of theory) of methyl 3-[3-(3-chlorobenzoyloxy)-phenyl]- 2-methoximinopropionate of melting point 65° C. are obtained.

PREPARATION OF THE STARTING COMPOUND

Example V-1

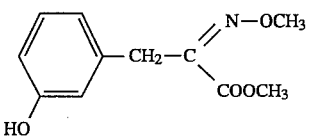

To 142.9 g (0.61 mol) of methyl 3-(3-hydroxyphenyl)-2-acetamidoacrylate in 600 ml of methanol there are added 50.6 g (0.61 mol) of O-methylhydroxylamine hydrochloride and then, dropwise and with stirring, 61 g (0.61 mol) of concentrated sulphuric acid, during which the temperature of the reaction mixture rises to 35° C. The mixture is stirred for 30 minutes at room temperature and then refluxed for 18 hours. For working up, the solvent is distilled off under a water pump vacuum, the residue is taken up in 600 ml of dichloromethane, washed twice with 300 ml of water each time, dried over sodium sulphate and concentrated in vacuo, and the residue is chromatographed on silica gel (eluent: dichloromethane/methanol 100:2.5) and subsequently crystallized from 150 ml of n-hexane/diisopropyl ether (9:1).

77.9 g (57% of theory) of methyl 3-(3-hydroxyphenyl)-2-methoximinopropionate of melting point 75° C. are obtained.

Example X-1

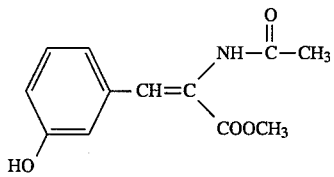

To 124.7 g (0.51 mol) of 4-(3-acetoxybenzylidene)-2-methyl- 2-oxazolin-5-one (compare DE 2,243,665) in 600 ml of methanol there is added 0.44 ml (0.005 mol) of 50 percent strength sodium hydroxide solution, the mixture is then stirred for 3 hours at 65° C., a further 4 ml (0.045 mol) of 50 percent sodium hydroxide solution are added, and the mixture is stirred for 16 hours at 20° C. For working up, 5 ml (0.05 mol) of concentrated hydrochloric acid are added, the solvent is distilled off, 500 ml of water are added, and the solid which has precipitated is filtered off with suction.

102.7 g (86% of theory) of methyl 3-(3-hydroxyphenyl)-2-acetamidoacrylate of melting point 115° C. are obtained.

The following 2-methoximinocarboxylic esters of the general formula (I) are obtained in a corresponding manner and following the general preparation instructions:

| Example No. | Ar | A | Physical properties |
|---|---|---|---|
| 4 | 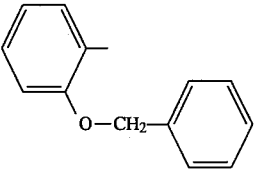 | —CH₂— | m.p.: 55° C. |
| 5 | 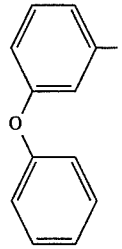 | —CH₂— | $n_D^{23}$: 1.5620 |
| 6 | 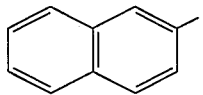 | —CH₂— | m.p.: 60° C. |
| 7 | 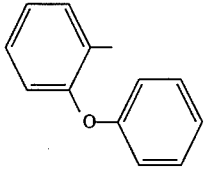 | —CH₂— | $n_D^{23}$: 1.5609 |
| 8 | 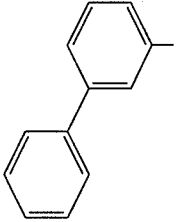 | —CH₂— | $n_D^{20}$: 1.5822 |
| 9 | 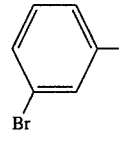 | —CH₂— | $n_D^{20}$: 1.5468 |
| 10 | 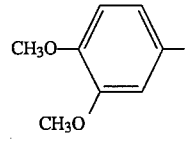 | —CH₂— | m.p.: 70° C. |
| 11 | 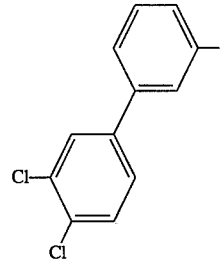 | —CH₂— | m.p.: 35° C. |

-continued
| Example No. | Ar | A | Physical properties |
|---|---|---|---|
| 12 | 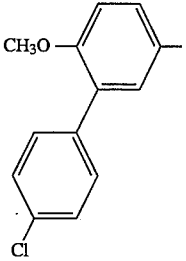 | —CH$_2$— | m.p.: 62° C. |
| 13 | 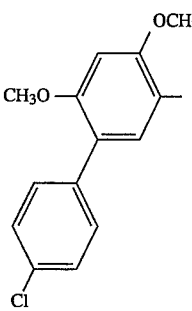 | —CH$_2$— | m.p.: 120° C. |
| 14 | 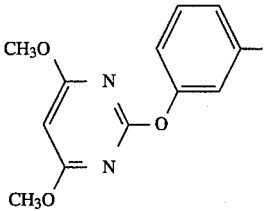 | —CH$_2$— | m.p.: 106° C. |
| 15 | 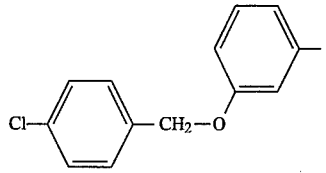 | —CH$_2$— | $n_D^{20}$: 1.5641 |
| 16 | 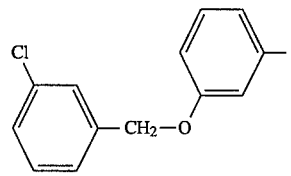 | —CH$_2$— | $n_D^{20}$: 1.5682 |
| 17 | 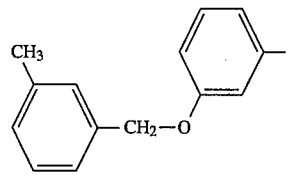 | —CH$_2$— | $n_D^{23}$: 1.5579 |
| 18 | 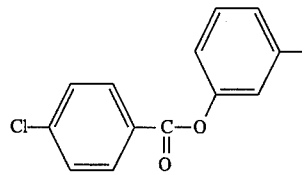 | —CH$_2$— | m.p.: 90° C. |

-continued

| Example No. | Ar | A | Physical properties |
|---|---|---|---|
| 19 | 3,4-dichlorobenzoate of (3-methylphenyl) | —CH$_2$— | m.p.: 104° C. |
| 20 | 2,5-dimethylbenzoate of (3-methylphenyl) | —CH$_2$— | m.p.: 56° C. |
| 21 | 4-(4-nitrophenylthio)benzoate of (3-methylphenyl) | —CH$_2$— | $n_D^{20}$: 1.6261 |
| 22 | 4-methylbenzoate of (3-methylphenyl) | —CH$_2$— | m.p.: 110° C. |
| 23 | 3,4-dimethoxybenzoate of (3-methylphenyl) | —CH$_2$— | m.p.: 100° C. |
| 24 | 1-naphthoate of (3-methylphenyl) | —CH$_2$— | m.p.: 60° C. |
| 25 | 2,4-dichlorobenzoate of (3-methylphenyl) | —CH$_2$— | m.p.: 70° C. |
| 26 | 3-methylbenzoate of (3-methylphenyl) | —CH$_2$— | m.p.: 68° C. |

-continued

| Example No. | Ar | A | Physical properties |
|---|---|---|---|
| 27 | 2-naphthyl-C(=O)O-(3-methylphenyl) | —CH$_2$— | m.p.: 96° C. |
| 28 | 3-methoxyphenyl-C(=O)O-(3-methylphenyl) | —CH$_2$— | $n_D^{20}$: 1.5592 |
| 29 | 4-tert-butylphenyl-C(=O)O-(3-methylphenyl) | —CH$_2$— | $n_D^{20}$: 1.5448 |
| 30 | 3-chloro-4-methylphenyl-C(=O)O-(3-methylphenyl) | —CH$_2$— | m.p.: 86° C. |
| 31 | 3-(dichloromethyl)phenyl-C(=O)O-(3-methylphenyl) | —CH$_2$— | $n_D^{20}$: 1.5699 |
| 32 | 4-chloro-3-cyanophenyl-C(=O)O-(3-methylphenyl) | —CH$_2$— | m.p.: 100° C. |
| 33 | 3-phenoxyphenyl (3-methyl) | $\underset{\underset{CH_3}{\vert}}{-N-}$ | $n_D^{20}$: 1.5753 |
| 34 | 3-(allyloxy)phenyl (3-methyl) | —CH$_2$— | $n_D^{23}$: 1.5261 |

-continued

| Example No. | Ar | A | Physical properties |
|---|---|---|---|
| 35 | 4-(Cl₂CH-)C₆H₄-C(=O)-O-(3-methylphenyl) | —CH₂— | m.p.: 60° C. |
| 36 | 3-(CCl₃)C₆H₄-C(=O)-O-(3-methylphenyl) | —CH₂— | $n_D^{20}$: 1.5738 |
| 37 | 3-Br-C₆H₄-C(=O)-O-(3-methylphenyl) | —CH₂— | m.p.: 92° C. |
| 38 | 4'-O₂N-biphenyl-4-C(=O)-O-(3-methylphenyl) | —CH₂— | m.p.: 130° C. |
| 39 | 3-(CH₃-C(=O)-O-)C₆H₄-C(=O)-O-(3-methylphenyl) | —CH₂— | m.p.: 96° C. |
| 40 | 4-Cl-C₆H₄-C(=O)-NH-C₆H₄-4-C(=O)-O-(3-methylphenyl) | —CH₂— | m.p.: 154° C. |
| 41 | biphenyl-4-C(=O)-O-(3-methylphenyl) | —CH₂— | m.p.: 95° C. |
| 42 | 2-Cl-C₆H₄-C(=O)-NH-C₆H₄-4-C(=O)-O-(3-methylphenyl) | —CH₂— | m.p.: 142° C. |

-continued
| Example No. | Ar | A | Physical properties |
|---|---|---|---|
| 43 | 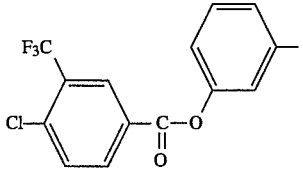 | —CH$_2$— | m.p.: 58° C. |
| 44 | 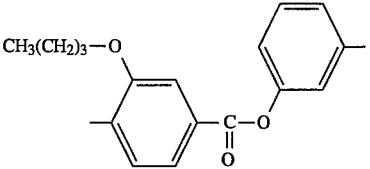 | —CH$_2$— | m.p.: 38° C. |
| 45 | 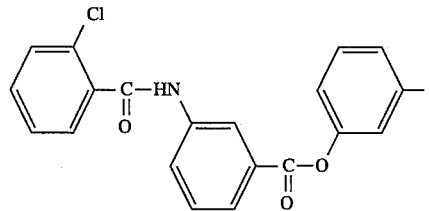 | —CH$_2$— | m.p.: 60° C. |
| 46 | 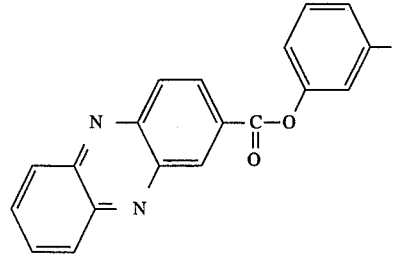 | —CH$_2$— | m.p.: 178° C. |
| 47 | 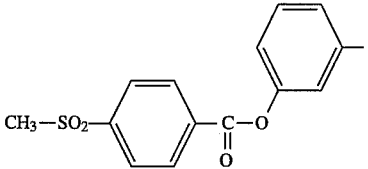 | —CH$_2$— | m.p.: 160° C. |
| 48 | 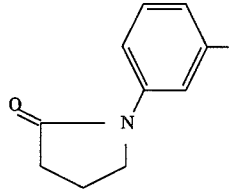 | —N— <br> \| <br> CH$_3$ | m.p.: 88°–92° C. |
| 49 | 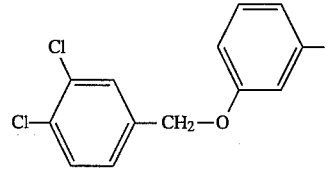 | —CH$_2$— | m.p.: 78° C. |

-continued
| Example No. | Ar | A | Physical properties |
|---|---|---|---|
| 50 | 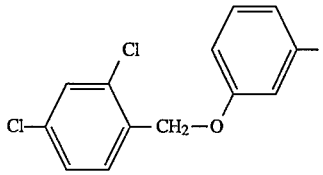 | —CH₂— | $n_D^{20}$: 1.5695 |
| 51 | 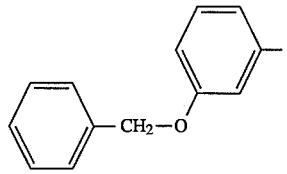 | —CH₂— | $n_D^{20}$: 1.5471 |
| 52 | 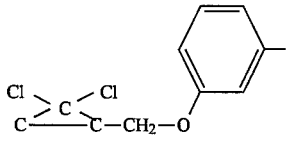 | —CH₂— | $n_D^{20}$: 1.5363 |
| 53 | 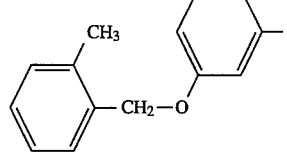 | —CH₂— | $n_D^{20}$: 1.5598 |
| 54 | 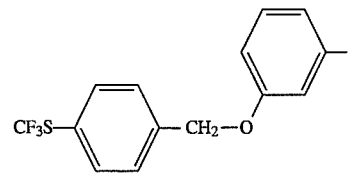 | —CH₂— | $n_D^{20}$: 1.5394 |
| 55 | 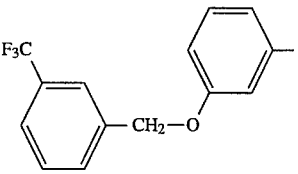 | —CH₂— | $n_D^{20}$: 1.5214 |
| 56 | 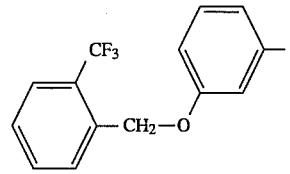 | —CH₂— | $n_D^{20}$: 1.5233 |
| 57 | 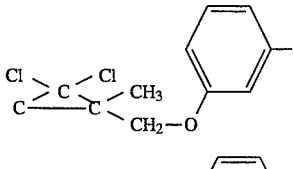 | —CH₂— | $n_D^{20}$: 1.5324 |
| 58 | 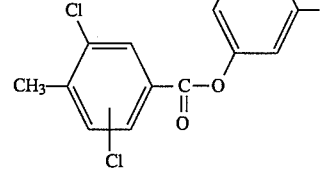 | —CH₂— | $n_D^{20}$: 1.5711 (micture of isomers) |

-continued
| Example No. | Ar | A | Physical properties |
|---|---|---|---|
| 59 | 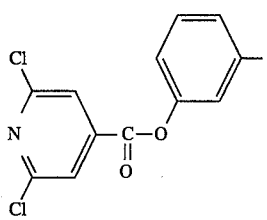 | —CH₂— | m.p. 120° C. |
| 60 | 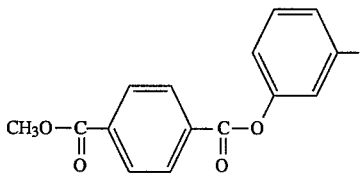 | —CH₂— | m.p. 192° C. |
| 61 | 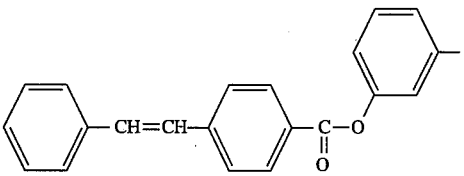 | —CH₂— | m.p. 106° C. |
| 62 | 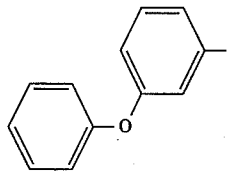 | —N—<br>\|<br>CH₃ | |
| 63 | 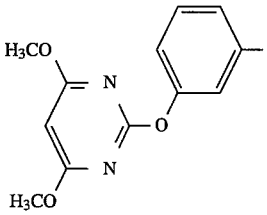 | —CH₂— | m.p. 72° C. |
| 64 | 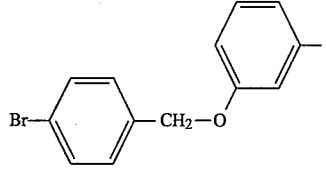 | —CH₂— | m.p. 68° C. |
| 65 | 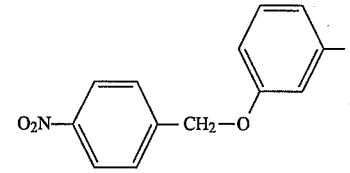 | —CH₂— | m.p. 78° C. |
| 66 | 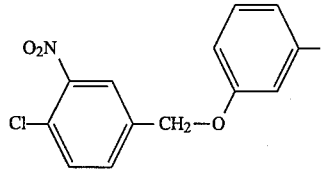 | —CH₂— | m.p. 71° C. |

-continued

| Example No. | Ar | A | Physical properties |
|---|---|---|---|
| 67 | 2,3-dichlorophenyl-CH₂-O-(3-phenyl) | —CH₂— | m.p. 50° C. |
| 68 | 2-chlorophenyl-CH₂-O-(3-phenyl) | —CH₂— | $n_D^{20}$: 1.5679 |
| 69 | 5,6,7,8-tetrahydronaphthyl-O-(3-phenyl) | —CH₂— | $n_D^{20}$: 1.5748 (mixture of isomers) |
| 70 | 4-cyanophenyl-CH₂-O-(3-phenyl) | —CH₂— | m.p. 70° C. |
| 71 | 4-benzoylphenyl-CH₂-O-(3-phenyl) | —CH₂— | $n_D^{20}$: 1.5978 |
| 72 | 4-biphenyl-CH₂-O-(3-phenyl) | —CH₂— | m.p. 80° C. |
| 73 | 4-cyclohexylphenyl-CH₂-O-(3-phenyl) | —CH₂— | $n_D^{20}$: 1.5598 |
| 74 | 3-bromophenyl-CH₂-O-(3-phenyl) | —CH₂— | $n_D^{20}$: 1.5807 |

-continued

| Example No. | Ar | A | Physical properties |
|---|---|---|---|
| 75 | 4-(EtO-C(=O))-C6H4-CH2-O-(3-C6H4)- | —CH2— | m.p. 58° C. |
| 76 | 3-(MeO)-C6H4-CH2-O-(3-C6H4)- | —CH2— | $n_D^{20}$: 1.5648 |
| 77 | 4-(H3C)-C6H4-CH2-O-(3-C6H4)- | —CH2— | m.p. 70° C. |
| 78 | (H3C)2-C6H3-CH2-O-(3-C6H4)- | —CH2— | $n_D^{20}$: 1.5603 (mixture of isomers) |
| 79 | 2,5-(H3C)2-C6H3-CH2-O-(3-C6H4)- | —CH2— | $n_D^{20}$: 1.5579 |
| 80 | 2-CH3,4-CH3-C6H3-CH2-O-(3-C6H4)- | —CH2— | m.p. 58° C. |
| 81 | 3,4-(H3C)2-C6H3-CH2-O-(3-C6H4)- | —CH2— | $n_D^{20}$: 1.5599 |
| 82 | 3-(PhO)-C6H4-CH2-O-(3-C6H4)- | —CH2— | $n_D^{20}$: 1.5830 |

-continued
| Example No. | Ar | A | Physical properties |
|---|---|---|---|
| 83 | 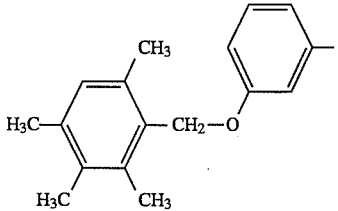 | —CH$_2$— | m.p. 86° C. |
| 84 | 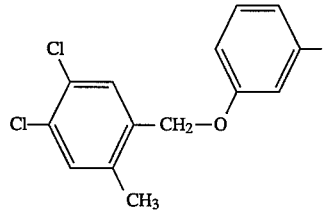 | —CH$_2$— | m.p. 78° C. |
| 85 | 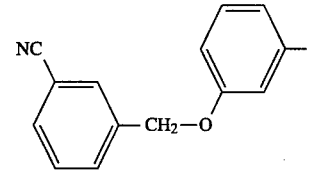 | —CH$_2$— | m.p. 84° C. |
| 86 | 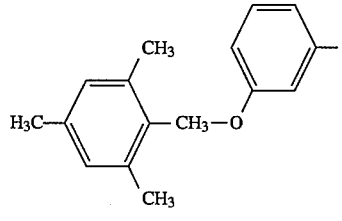 | —CH$_2$— | $n_D^{20}$: 1.5710 |
| 87 | 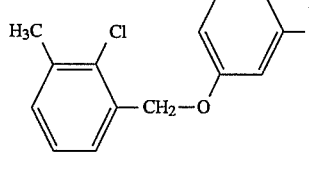 | —CH$_2$— | m.p. 86° C. |
| 88 | 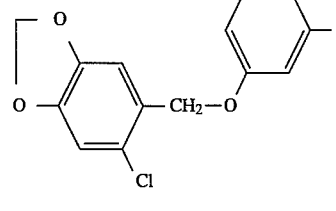 | —CH$_2$— | m.p. 76° C. |
| 89 | 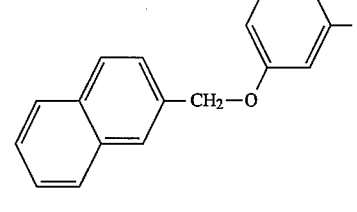 | —CH$_2$— | m.p. 84° C. |

-continued

| Example No. | Ar | A | Physical properties |
|---|---|---|---|
| 90 | 1-naphthyl-CH₂-O-(3-substituted phenyl) | —CH₂— | $n_D^{20}$: 1.6059 |
| 91 | 2-(2-oxyethyl)benzyl-O-(3-substituted phenyl) | —CH₂— | $n_D^{20}$: 1.5707 |
| 92 | 4-(F₃C)-C₆H₄-CH₂-O-(3-substituted phenyl) | —CH₂— | m.p. 60° C. |
| 93 | 4-(F₃CO)-C₆H₄-CH₂-O-(3-substituted phenyl) | —CH₂— | $n_D^{20}$: 1.5162 |
| 94 | 4-(CH₃-SO₂)-C₆H₄-CH₂-O-(3-substituted phenyl) | —CH₂— | m.p. 80° C. |
| 95 | 2-Cl-C₆H₄-CH₂-O-(3-substituted phenyl)-CH₂-O-(3-substituted phenyl) | —CH₂— | $n_D^{20}$: 1.5871 |
| 96 | benzothiadiazol-CH₂-O-(3-substituted phenyl) | —CH₂— | m.p. 72° C. |

-continued

| Example No. | Ar | A | Physical properties |
|---|---|---|---|
| 97 | (triazole-thiadiazole with N-CH₃, C(=O)-NH linked to phenyl-CH₂-O-phenyl) | —CH₂— | m.p. 110° C. |
| 98 | CH₃O—N=CH—(phenyl)—CH₂—O—(phenyl)— | —CH₂— | m.p. 74° C. |
| 99 | (biphenyl)—CH=CH—(phenyl)—C(=O)O—(phenyl)— | —CH₂— | m.p. 196° C. |
| 100 | CH₃—(CH₂)₃—O—C(=O)—(phenyl)—C(=O)—O—(phenyl)— | —CH₂— | m.p. 130° C. |
| 101 | (3,4-dimethylbiphenyl)— | —CH₂— | m.p. 80° C. |
| 102 | (pyrimidin-2-yl)—O—(phenyl)— | —CH₂— | Fp.: 72° C. |

-continued

| Example No. | Ar | A | Physical properties |
|---|---|---|---|
| 103 | (4-chloro-6-trifluoromethylpyrimidin-2-yloxy)-phenyl | —CH$_2$— | Fp.: 68° C. |
| 104 | (4-trifluoromethylpyrimidin-2-yloxy)-phenyl | —CH$_2$— | Fp.: 90° C. |
| 105 | [4-(4-chlorophenyl)-6-chloro-1,3,5-triazin-2-yloxy]-phenyl | —CH$_2$— | Fp.: 120° C. |
| 106 | [4-(1-methylpropoxy)-6-chloro-1,3,5-triazin-2-yloxy]-phenyl | —CH$_2$— | $n_D^{20}$: 1.5396 |
| 107 | (5-chloropyrimidin-2-yloxy)-phenyl | —CH$_2$— | Fp.: 104° C. |
| 108 | [2-chloro-6-phenylpyrimidin-4-yloxy]-phenyl | —CH$_2$— | Fp.: 180° C. |
| 109 | (2-chloro-6-methylpyrimidin-4-yloxy)-phenyl | —CH$_2$— | Fp.: 94° C. |

-continued

| Example No. | Ar | A | Physical properties |
|---|---|---|---|
| 110 | 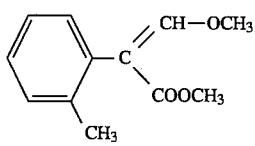 | —CH₂— | Fp.: 82° C. |

USE EXAMPLES

In the use examples which follow the compound listed below was employed as comparison substance:

$$\underset{\underset{CH_3}{}}{\text{C}_6H_4}-C(=CH-OCH_3)-COOCH_3 \quad (A)$$

methyl 3-methoxy-2-(2-methylphenyl)-acrylate (disclosed in European Patent 178,826).

Example A

Pyrenophora teres test (barley)/protective

Solvent: 100 parts by weight of dimethylformamide

Emulsifier: 0.25 part by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist.

After the spray coating has dried on, the plants are sprayed with a conidia suspension of *Pyrenophora teres*. The plants remain in an incubation cabin at 20° C. and 100% relative atmospheric humidity for 48 hours.

The plants are placed in a greenhouse at a temperature of about 20° C. and a relative atmospheric humidity of about 80%.

Evaluation is carried out 7 days after the inoculation.

In this test, a clearly superior activity compared with the prior art is shown, for example, by the compounds of the following preparation examples: 9, 10 and 12.

Example B

Erysiphe test (wheat)/protective

Solvent: 100 parts by weight of dimethylformamide

Emulsifier: 0.25 part by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are sprayed with spores of Erysiphe graminis f.sp. tritici.

The plants are placed in a greenhouse at a temperature of about 20° C. and a relative atmospheric humidity of about 80%, in order to promote the development of mildew pustules.

Evaluation is carried out 7 days after the inoculation.

In this test, a clearly superior activity compared with the prior art is shown, for example, by the compounds of the following preparation examples: 1, 4, 5, 6, 8 and 11.

Example C

Erysiphe test (barley)/protective

Solvent: 100 parts by weight of dimethylformamide

Emulsifier: 0.25 part by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are sprayed with spores of Erysiphe graminis f.sp. hordei.

The plants are placed in a greenhouse at a temperature of about 20° C. and a relative atmospheric humidity of about 80%, in order to promote the development of mildew pustules.

Evaluation is carried out 7 days after the inoculation.

In this test, a clearly superior activity compared with the prior art is shown, for example, by the compounds of the following preparation examples: 1, 4, 5, and 11.

Example D

Venturia test (apple)/protective

Solvent: 4.7 parts by weight of acetone

Emulsifier: 0.3 part by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous conidia suspension of the apple scab causative organism (*Venturia inaequalis*) and then remain in an incubation cabin at 20° C. and 100% relative atmospheric humidity for 1 day.

The plants are then placed in a greenhouse at 20° C. and a relative atmospheric humidity of about 70%.

Evaluation is carried out 12 days after the inoculation.

In this test, a clearly superior activity compared with the prior art is shown, for example, by the compounds of the following preparation examples: 1 and 11.

It will be understood that the specification and examples are illustrative but not limitative of the present invention and that other embodiments within the spirit and scope of the invention will suggest themselves to those skilled in the art.

We claim:

1. A 2-methoximinocarboxylic ester of the formula

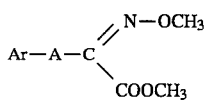

(I)

in which

Ar represents

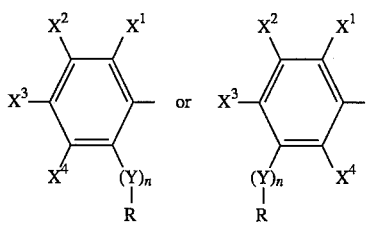

and

A represents —CH$_2$—;

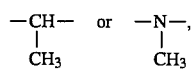

where

Y represents

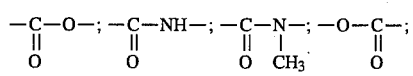

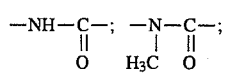

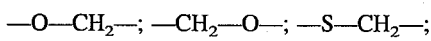

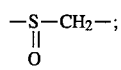

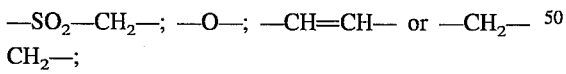

n represents the number 0 or 1,

R represents optionally substituted heteroaryl, and $X^1$, $X^2$, $X^3$ and $X^4$ each independently represents hydrogen, halogen, hydroxyl or methoxy, but in the event that $X^2$ represents bromine $X^3$ does not simultaneously represent hydroxyl or methoxy.

2. A methoximinocarboxylic ester according to claim 1, in which

Ar represents

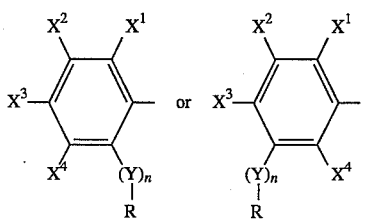

and

A represents one —CH$_2$—;

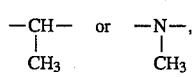

where

Y represents

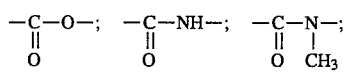

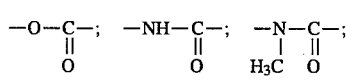

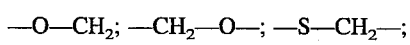

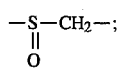

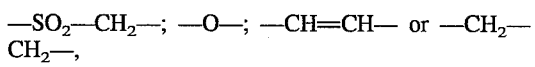

n represents the number 0 or 1,

R represents heteroaryl which has 2 to 9 carbon atoms and 1 to 5 identical or different hetero atoms and which is optionally substituted by substituents independently selected from the group consisting of halogen and in each case straight-chain or branched alkyl or alkoxy each of which has 1 to 6 carbon atoms; and $X^1$, $X^2$, $X^3$ and $X^4$ each independently represents hydrogen, fluorine, chlorine bromine, iodine, hydroxyl or methoxy, but in the event that $X^2$ represents bromine $X^3$ does not simultaneously represent hydroxyl or methoxy.

3. A 2-methoximinocarboxylic ester according to claim 1, in which

Ar represents

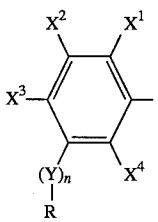

and

A represents —CH$_2$—;

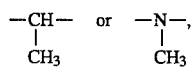

where

Y represents

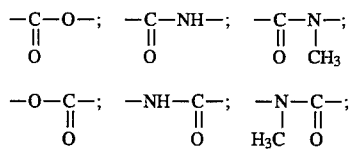

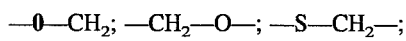

—O—CH$_2$; —CH$_2$—O—; —S—CH$_2$—;

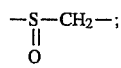

—SO$_2$—CH$_2$— ; —O—; —CH=CH— or —CH$_2$—CH$_2$—, n represents the number 0 or 1, R represents heteroaryl which has 2 to 9 carbon atoms and 1 to 4 identical or different hetero atoms and which is optionally monosubstituted to trisubstituted by substituents independently selected from the group consisting of fluorine, chlorine, bromine and in each case straight-chain or branched alkyl or alkoxy each of which has 1 to 4 carbon atoms; and X$^1$, X$^2$, X$^3$ and X$^4$ each independently represents hydrogen, chlorine, bromine, hydroxyl or methoxy, but in the event that X$^2$ represents bromine X$^3$ does not simultaneously represent hydroxyl or methoxy.

4. A compound according to claim 1, wherein A is —CH$_2$— and Ar is a selected from the group consisting of:

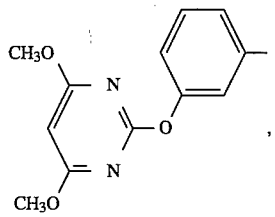

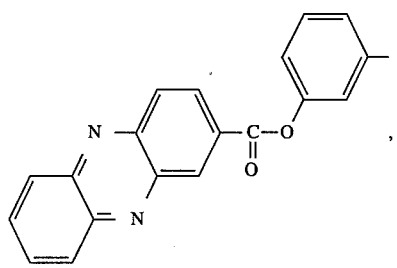

-continued

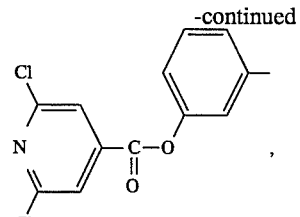

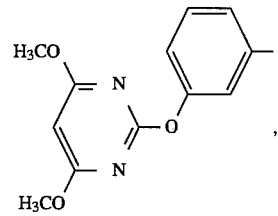

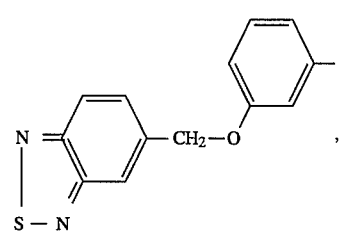

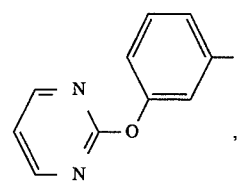

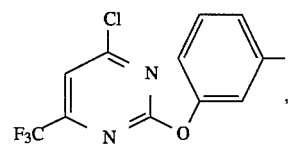

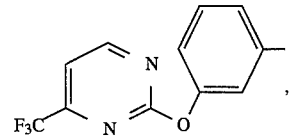

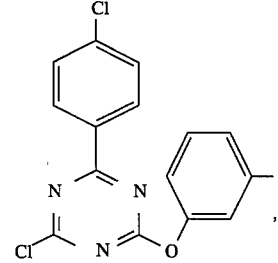

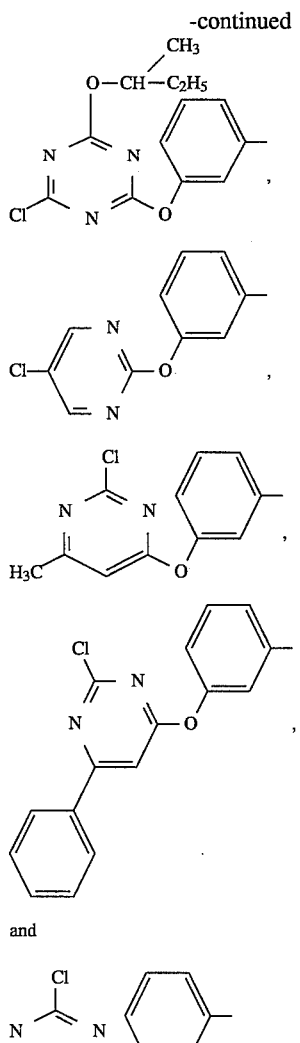

and

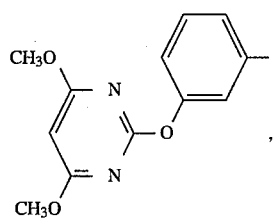

5. A fungicidal composition comprising a fungicidally effective amount of a compound according to claim 1 and a diluent.

6. A method of combatting fungi which comprises applying to such fungi or to a locus from which it is desired to exclude such fungi a fungicidally effective amount of a compound according to claim 1.

7. The method according to claim 6, wherein the compound is one in which A is —CH$_2$— and Ar is a selected from the group consisting of:

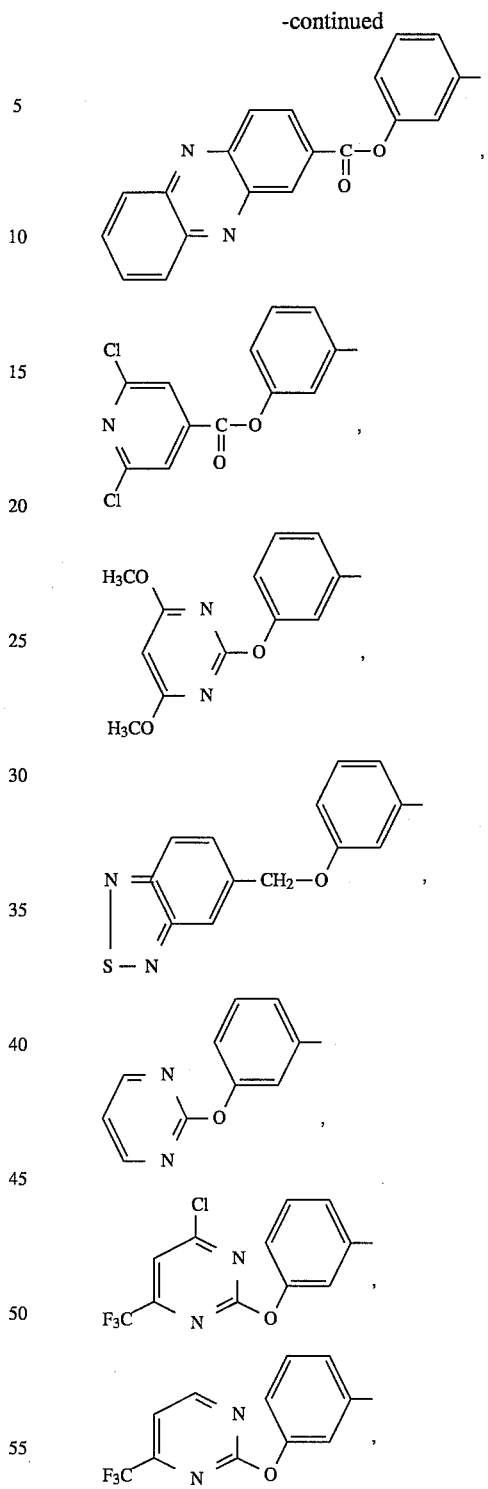

-continued

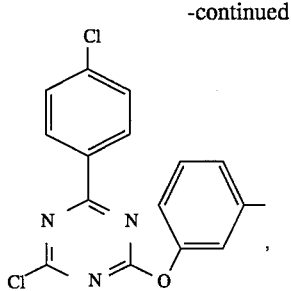,

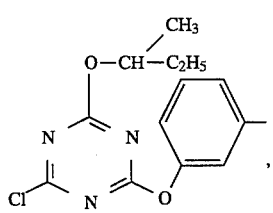,

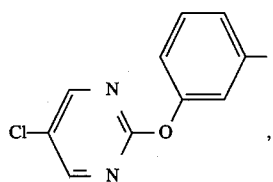,

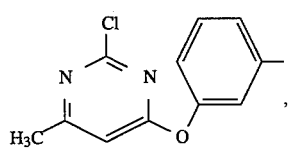,

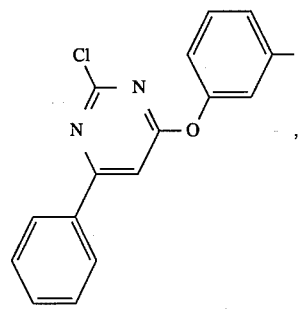

and

-continued

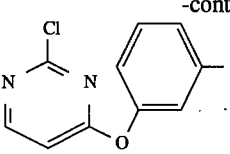

8. A compound of the formula

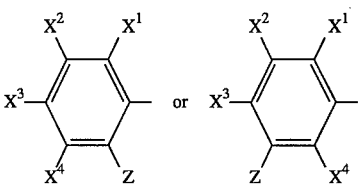 (V)

in which

R$^1$ represents hydrogen or methyl and

Ar$^2$ represents

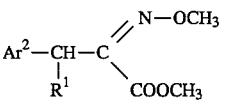

where

Z in each case represents hydroxyl, amino or N-methylamino and

X$^1$, X$^2$, X$^3$ and X$^4$ each independently represents hydrogen, halogen, hydroxyl or methoxy, but in the event that X$^2$ represents bromine X$^3$ does not simultaneously represent hydroxyl or methoxy.

* * * * *

UNITED STATES PATENT AND TRADEMARK OFFICE
CERTIFICATE OF CORRECTION

PATENT NO. : 5,464,809
DATED : November 7, 1995
INVENTOR(S) : Kramer, et al.

It is certified that error appears in the above-indentified patent and that said Letters Patent is hereby corrected as shown below:

Col. 53, line 20      Delete " -O-CH$_2$ " and substitute
                      -- -O-CH$_2$ --

Col. 53, claim 4      Delete " a "
line 42

Col. 54, line 28      Insert -- 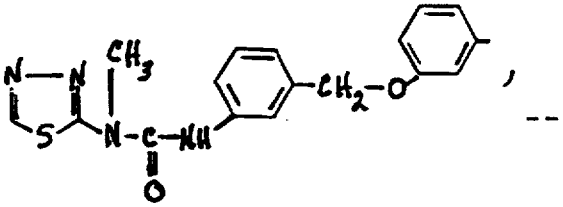 --

Col. 55, line 52      Delete " a "

UNITED STATES PATENT AND TRADEMARK OFFICE
CERTIFICATE OF CORRECTION

PATENT NO. : 5,464,809
DATED : November 7, 1995
INVENTOR(S) : Kramer, et al.

It is certified that error appears in the above-indentified patent and that said Letters Patent is hereby corrected as shown below:

Col. 56, line 38    Insert -- 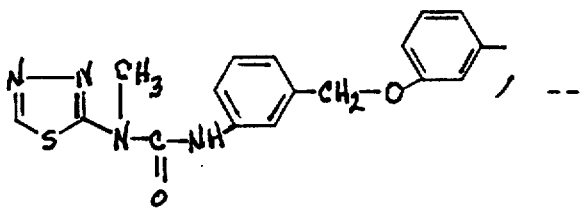 --

Signed and Sealed this

Thirtieth Day of July, 1996

Attest:

BRUCE LEHMAN

Attesting Officer    Commissioner of Patents and Trademarks